(12) United States Patent
Felix

(10) Patent No.: US 10,847,007 B1
(45) Date of Patent: Nov. 24, 2020

(54) INTERACTIVE MONITORING SYSTEM

(71) Applicant: Thembisa Felix, Brooklyn, NY (US)

(72) Inventor: Thembisa Felix, Brooklyn, NY (US)

(*) Notice: Subject to any disclaimer, the term of this patent is extended or adjusted under 35 U.S.C. 154(b) by 0 days.

(21) Appl. No.: 16/502,306

(22) Filed: Jul. 3, 2019

(51) Int. Cl.
*G08B 21/02* (2006.01)
*G08B 5/22* (2006.01)

(52) U.S. Cl.
CPC .......... *G08B 21/0291* (2013.01); *G08B 5/22* (2013.01); *G08B 21/028* (2013.01); *G08B 21/0236* (2013.01); *G08B 21/0277* (2013.01)

(58) Field of Classification Search
CPC ............ G08B 21/0236; G08B 21/0277; G08B 21/028; G08B 21/0291; G08B 5/22; G06F 3/017; G06F 3/0482; G06F 3/0488; G06F 3/167; G10L 15/22
See application file for complete search history.

(56) References Cited

U.S. PATENT DOCUMENTS

| 6,043,747 | A | 3/2000 | Altenhofen |
| 7,049,968 | B2 | 5/2006 | Fitzgerald |
| 2017/0068322 | A1* | 3/2017 | Steinberg ................. G06F 3/005 |
| 2017/0132922 | A1* | 5/2017 | Gupta .................... G06F 3/0482 |
| 2018/0349678 | A1* | 12/2018 | Koskan ............... G06K 9/00604 |
| 2019/0095090 | A1* | 3/2019 | Proctor ............... G06F 3/04883 |
| 2019/0118104 | A1* | 4/2019 | Su ........................... A63H 3/02 |
| 2019/0251622 | A1* | 8/2019 | Wiedmeyer ......... G06Q 30/0623 |
| 2019/0369699 | A1* | 12/2019 | Pathak .................. G06F 1/3206 |

* cited by examiner

*Primary Examiner* — Orlando Bousono
(74) *Attorney, Agent, or Firm* — Sanchelima & Associates, P.A.; Christian Sanchelima; Jesus Sanchelima

(57) ABSTRACT

An interactive monitoring system, comprising an object located in proximity to a first user and a remote display device, communicably coupled with the object over a communication network is disclosed. The object comprises a plurality of sensors that detects a generic event performed by the first user and cause a plurality of electronic units located on the object to activate based on the detected generic event performed by the first user. Remote display device display a field-of-view (FOV) captured by a first electronic unit of the activated plurality of electronic units. A second user associated with the remote display device communicates with the first user associated with the object over the communication network. The interactive monitoring system is Bluetooth compatible and the speakers can be found on both ears.

12 Claims, 3 Drawing Sheets

INTERACTIVE MONITORING SYSTEM

BACKGROUND OF THE INVENTION

1. Field of the Invention

The present disclosure relates to an interactive monitoring system. More particularly, the present disclosure relates to an interactive system for monitoring and engaging a child.

2. Description of the Related Art

Many monitoring apparatuses, such as baby monitors, are widely used all over the world to assist parents, guardians, and supervisors to observe and monitor those under their care, such as infants, toddlers, or special children with developmental disabilities.

Several designs for interactive monitoring apparatus have been presented in the past. None of them, however, presents a simple and interactive monitoring system that is user friendly, easy to install, and a great safety system.

Applicant believes that a related reference corresponds to U.S. Pat. No. 7,049,968B2 filed by Karen Fitzgerald which discloses a baby monitor system responsive to receiving a signal representative of an audible sound transmitted from the parent unit and the parent unit is responsive to receiving a signal representative of an audible sound transmitted from the baby unit. The disclosed method includes the steps of receiving a signal representative of an audible sound at a baby unit from a parent unit, receiving a signal representative of an audible sound at a parent unit from a baby unit, and actuating a soothing unit included in the baby unit.

Applicant further believes that another related reference corresponds to U.S. Pat. No. 6,043,747A filed by Cynthia L. Altenhofen discloses a baby monitor system having a parent unit and a baby with a two-way radio frequency communications link established therebetween. The baby monitor system also includes a message storage mechanism that allows a care giver to record a soothing message for playback to the baby in response to activation of a play switch. Use of the recorded message allows the care giver to provide the baby with a soothing message even when the care giver is in an ambient noise environment, such as a shower, that could startle are irritate the baby.

Other documents describing the closest subject matter provide for a number of more or less complicated features that fail to solve the problem in an efficient and economical way. None of these patents suggest the novel features of the present invention.

SUMMARY OF THE INVENTION

It is an object of the present invention to provide an interactive monitoring system, comprising an object located in proximity to a first user and a remote display device, communicably coupled with object over communication networks. Communication network may be a long distance or short distance wireless network.

It is another object of the present invention to provide an interactive monitoring system where the object comprises a plurality of sensors configured to detect a generic event performed by first user and activate a plurality of electronic units located on object based on detected generic event performed by first user. Plurality of sensors is configured to deactivate plurality of electronic units when object and remote display device are within a pre-defined proximity. Plurality of sensors may comprise at least motion activated camera sensor, voice sensor, and light sensor.

It is still another object of the present invention to provide an interactive monitoring system with a remote display device is configured to display a field-of-view (FOV) captured by a first electronic unit of activated plurality of electronic units, wherein a second user associated with remote display device communicates with first user associated with object, over communication network.

It is yet another object to provide an interactive monitoring system where first user may be an infant, a toddler, a young child, or a user who needs continuous supervision. Second user may be a parent, a guardian, or a supervisor. Object may be a toy, a soft toy, or an article constantly engaged with first user.

It is another object of the present invention to include a first electronic unit corresponding to an image capturing device. A second electronic unit of activated plurality of electronic units corresponds to a light display assembly comprising a plurality of light units, wherein plurality of light units is energized based on one of a plurality of pre-defined patterns. A third electronic unit of activated plurality of electronic units corresponds to one or more audio output devices, wherein one or more audio output devices are configured to render one of a plurality of pre-defined music files, wherein a fourth device of activated plurality of electronic units corresponds to one or more audio input devices, wherein one or more audio input devices are configured to receive voice input provided by first user.

It is another object of the present invention to provide an interactive monitoring system wherein the object further comprises a microprocessor configured to receive a voice input generated by first user via an audio input device, retrieve a response signal from a memory unit based on received voice input, and render response signal over an audio output device. Microprocessor is further configured to generate an alert notification for remote display device based on one or more critical events.

Further objects of the invention will be brought out in the following part of the specification, wherein detailed description is for the purpose of fully disclosing the invention without placing any limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
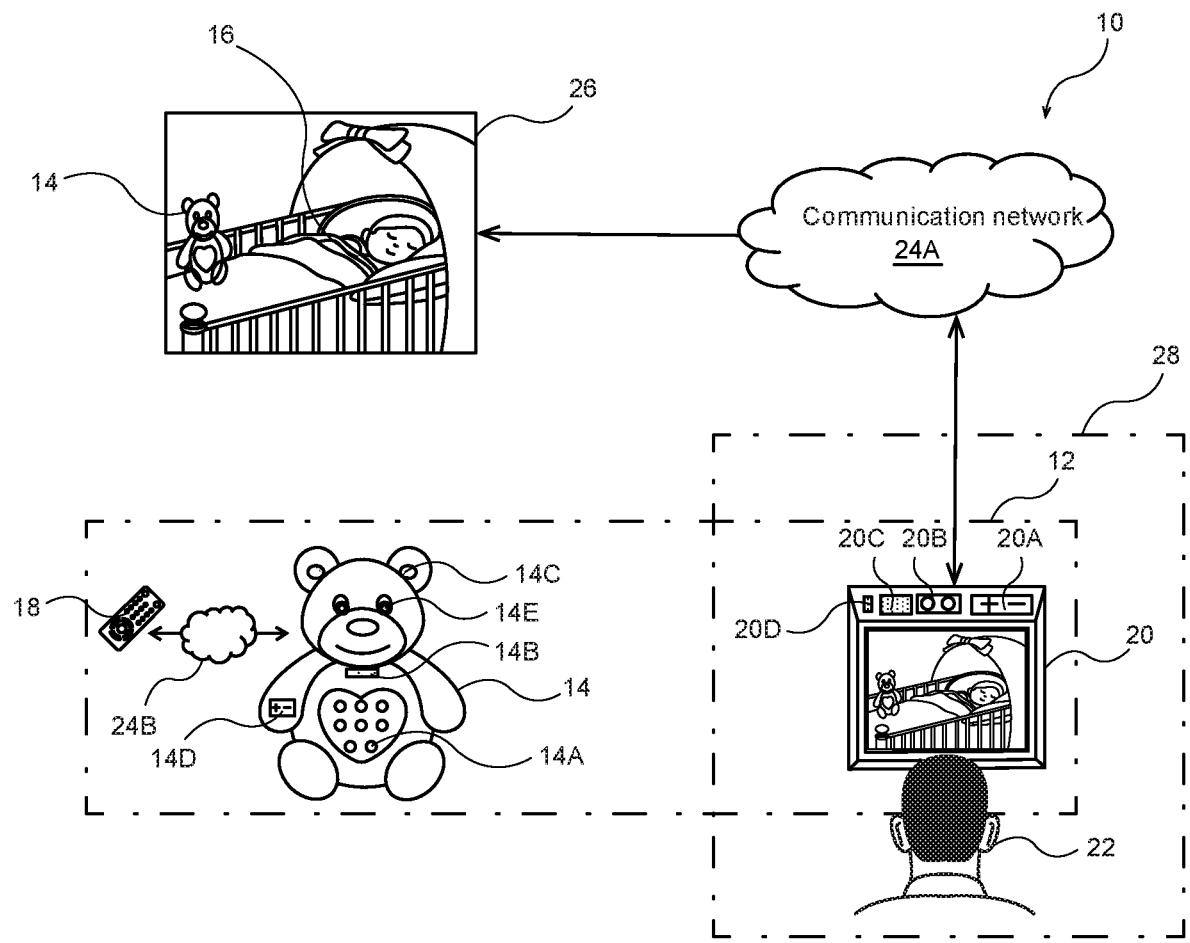
FIG. 1 represents an interactive monitoring system 12 of present invention in its operating environment 10, according to an embodiment described herein.

Referring now to the drawings, FIGS. 1-3, where the present invention is generally referred to with numeral 12, it can be observed that an interactive monitoring system, in accordance with one embodiment, is provided that includes various components, a described hereinafter.

FIG. 1 illustrates interactive monitoring system 12 of the present invention in its operating environment 10, which further includes object 14, remote control device 18, and remote display device 20. Object 14 further includes a light display assembly 14A, a first microphone 14B, a first set of speakers 14C, and a first set of volume controls 14D. Remote display device 20 further includes power on/off switches 20A, a second microphone 20B, a second set of speakers 20C, and a second set of volume controls 20D. Object 14 may be associated with first user 16 at location 26. Remote display device 20 may be associated with second user 22 at location 28. Remote display device 20 may be communicably coupled with object 14 over a long distance communication network 24A. Remote control device 18 may be communicably coupled with object 14 over a short distance communication network 24B. Remote control device 18 may be configured to pre-set and/or adjust various controls, such as light display assembly 14A, first microphone 14B, first set of speakers 14C, and first set of volume controls 14D, located on object 14.

In operation, object 14 may be located in proximity to first user 16 at location 26, such as a room. In an example embodiment, object 14, such as an interactive monitoring soft toy (like teddy bear), may be placed in cradle of a sleeping baby, i.e. first user 16. In other embodiments, first user 16 may be a toddler, a young child, or a user who needs continuous supervision. Based on category or age group of first user 16, object 14 may be a toy resembling a favorite animated or an article constantly engaged with first user 16.

In an embodiment, at very instant when there is a generic event, such as sudden movement/motion performed or voice of first user 16 uttered, by first user 16, a plurality of sensors 32 may detect generic event. In various examples, a motion activated camera sensor may detect sudden movement/motion of first user 16, and a voice sensor may detect and identify voice of first user 16. Plurality of sensors 32 may cause microprocessor 34 to activate a plurality of electronic units located on object 14.

In an embodiment, a first electronic unit from plurality of electronic units may be an image capturing device, such as a camera 14E, that gets activated due to movement/motion of first user 16 detected by motion activated camera sensor or voice of first user 16 detected by voice sensor. First electronic unit may capture a field-of-view (FOV) associated with first user 16 and communicate captured FOV to remote display device 20 associated with second user 22, over communication network 24A. In various examples, second user 22 may be a parent, a guardian, or a supervisor at different location 28, such as an office.

In an embodiment, remote display device 20, upon receiving FOV from first electronic unit, i.e. camera 14E, of object 14, displays FOV on a display screen of remote display device 20. In another embodiment, second user 22, by using second microphone 20B at remote display device 20, may speak to first user 16, via long distance communication network 24A. First user 16 may listen to second user 22 by using first set of speakers 14C. Alternatively, second user 22, by using second set of speakers 20C at remote display device 20, may listen to first user 16, via long distance communication network 24A. First user 16 may speak to second user 22 by using first microphone 14B.

It may be ensured that remote display device 20 has sufficient battery for performing operations, such as displaying, speaking, and listening. In case battery is low, a low battery indicator beeper, which activates when battery level of said remote display device is less than a threshold power level, is activated to indicate to second user 22, associated with remote display device 20, that remote display device 20 requires charging.

In an embodiment, until it is time for second user 22 to tend to first user 16, object 14 may be configured to engage first user 16 by various means. For example, a second electronic unit of said activated plurality of electronic units, which corresponds to a light display assembly 14A comprising a plurality of light units, such as mini LEDs, may be activated. Such plurality of light units may be energized based on one of a plurality of pre-defined patterns, i.e. a light show, pre-set by remote control device 18. Further, remote control device 18 may further control camera functions, voice recording options, and volume settings of object 14.

Further, a third electronic unit of the activated plurality of electronic units corresponds to one or more audio output devices, such as first set of speakers 14C, may be activated. Such one or more audio output devices are configured to render one of a plurality of pre-defined music files pre-set by remote control device 18.

Further, a fourth device of activated plurality of electronic units corresponds to one or more audio input devices, such as first microphone 14B, may be activated. Such one or more audio input devices are configured to receive voice input provided by first user 16. In such example, upon receiving voice input generated by first user 16, object 14 may retrieve a response signal from a memory unit 36 based on said received voice input. Accordingly, response signal may be rendered over audio output device, such as first set of speakers 14C.

In some embodiments, microprocessor 34 may be further configured to generate an alert notification for remote display device 20 based on one or more critical events. Such critical events may include emergency gestures, keywords such as "Ouch", a loud cry, or sudden change of emotions that may require immediate attention of second user 22. Such generated alert notifications are rendered by output devices, such as flash light, display screen, beeper, and/or the like, of remote display device 20. In response to alert notification, once second user 22 reaches within a pre-defined proximity, i.e. at location 26, of first user 16, microprocessor 34 may be configured to deactivate plurality of electronic units, i.e. light display assembly 14A, first microphone 14B, first set of speakers 14C, first set of volume controls 14D, and camera 14E, for power saving.

In certain embodiments, interactive monitoring system 12 further includes remote control device 18 that may be configured to control said plurality of electronic units. For example, during initial settings, second user 22 may set a desired energization pattern of plurality of light units, through remote control device 18. Further, second user 22 may set a desired music files for rendering, through remote control device 18.

Thus, based on activation by motion activated camera sensor, a catchy light show and soothing musical collection of interactive monitoring system 12 can capture attention of first user 16 and during such period, second user 22 is alerted and can arrange for things required to attend to needs of first user 16. Such interactive monitoring system 12 is more effective due to visual and audio stimulus. Interactive monitoring system 12 may be designed as several interactive animals or characters with interactive features, such as voice recorder, therapeutic light show display, music functions, motion sensors, and gesture-based controls, that can appeal to first user 16 or preferences of second user 22. In an embodiment, as described above, interactive monitoring system 12 may be voice activated where first user 16 may speak to object 14 and have object 14 speak to first user 16 using pre-determined questions that are appropriate to age of first user 16.

Figure 2:
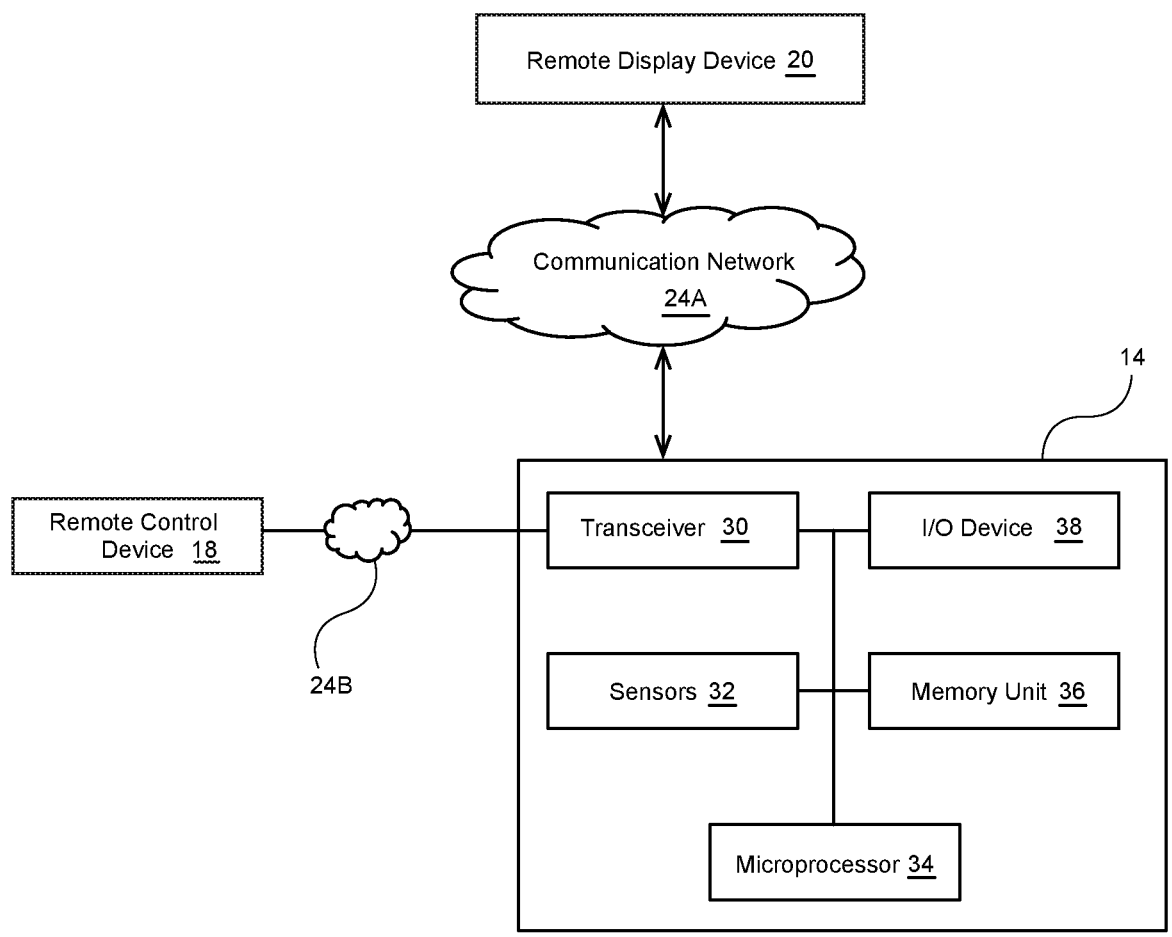
FIG. 2 demonstrates a block diagram of object 14, according to various embodiments described herein.

FIG. 2 demonstrates a block diagram of object 14, according to various embodiments described herein. Object 14 may include a transceiver 30, plurality of sensors 32, a microprocessor 34, a memory unit 36, and input/output (I/O) devices 38.

Transceiver 30 may be configured to implement known technologies to support wired or wireless communication of object 14 with communication networks 24A and 24B to transmit/receive signals and alerts to/from other devices, such as remote display device 20 and remote control device 18. In such case, object 14 is synchronized with one or more applications executing in other devices, e.g., remote display device 20. Such one or more applications provide an alert to second user 22 to perform suitable action, such as immediately attending to first user 16.

Sensors 32, such as motion sensor, a light sensor, camera sensor, may be configured to detect a generic event performed by first user 16, and cause microprocessor 34 to activate a plurality of electronic units, such as I/O devices 38, located on object 14 based on detected generic event performed by first user 16.

Microprocessor 34, as described above, may be configured to activate plurality of electronic units, such as I/O devices 38, located on object 14 based on generic event performed by first user 16. Microprocessor 34 may be further configured to receive voice input generated by first user 16 via an audio input device, such as first microphone 14B, and retrieve a response signal from memory unit 36 based on received voice input. Accordingly, microprocessor 34 renders response signal over an audio output device, such as first set of speakers 14C. Further, microprocessor 34 may be configured to generate an alert notification for remote display device 20 based on one or more critical events, for example when baby, i.e. first user 16, starts crying. Such generated alert notifications are rendered by I/O devices, such as flash light, display screen, beeper, and/or the like of remote display device 20. Microprocessor 34 may be an X86-based processor, a Reduced Instruction Set Computing (RISC) processor, an Application-Specific Integrated Circuit (ASIC) processor, a Complex Instruction Set Computing (CISC) processor, a microcontroller, a central processing unit (CPU), a digital signal processor (DSP), a graphics processor unit (GPU), a coprocessor, and/or other processors or integrated circuits.

Memory unit 36 may be configured to temporarily store various data, such as energization pattern of a light display assembly 14A and plurality of pre-defined music files. I/O devices 38 may comprise various input and output devices that may be configured to interface with object 14. Input devices of the I/O devices 38 may be further configured to receive one or more inputs from first user 16. Examples of input devices may include, but are not limited to, first microphone 14B, camera 14E, and/or plurality of sensors 32, such as a motion sensor, and/or a light sensor. Output devices of I/O devices 38 may display a light show, render voice of second user 22, render response signal retrieved from memory unit 3, and/or render one of a plurality of pre-defined music files. Examples of output devices may include, but are not limited to, light display assembly 14A and first set of speakers 14C.

Figure 3:
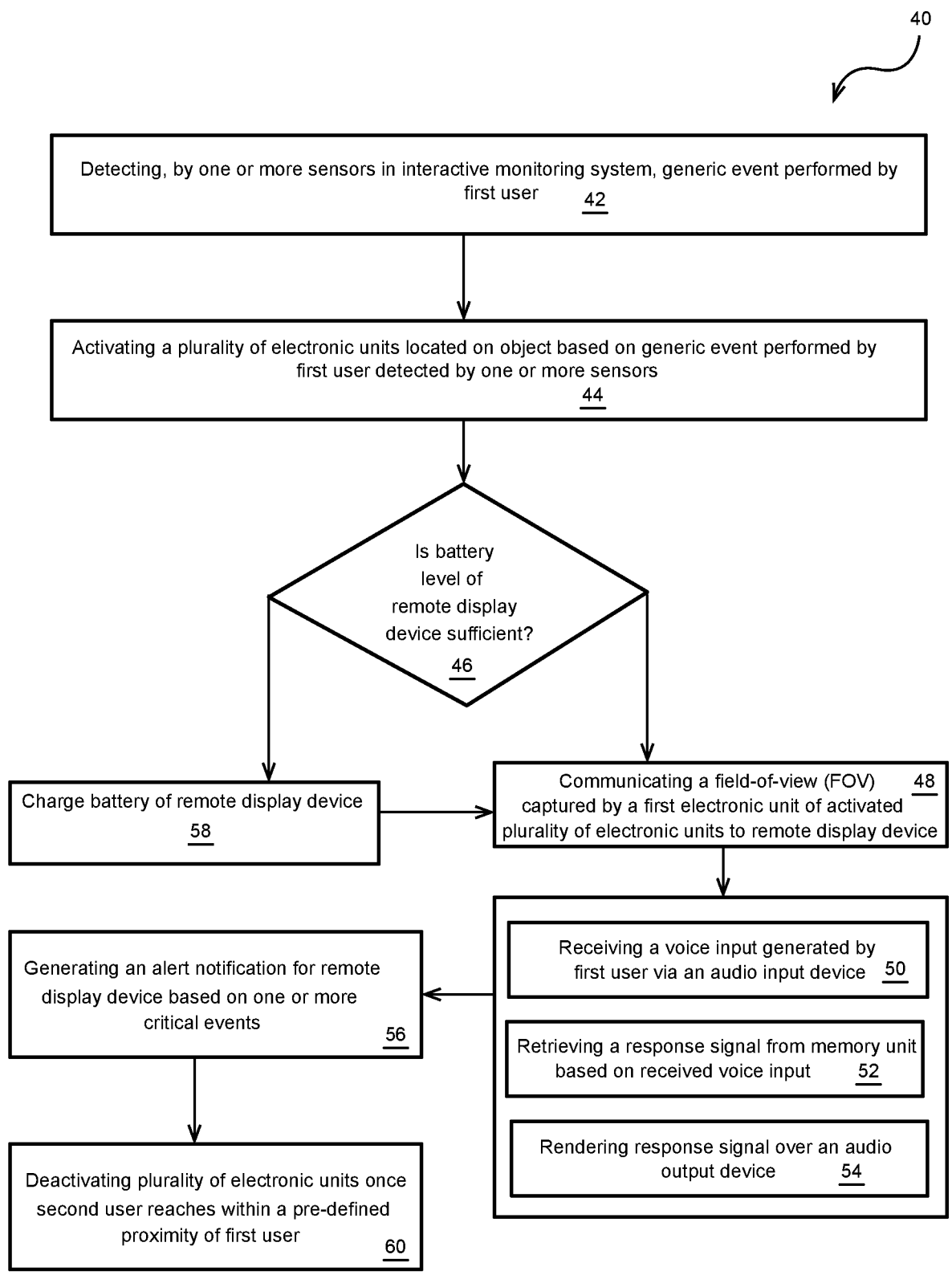
FIG. 3 is a flowchart for illustrating a method implemented by interactive monitoring system 12, according to an embodiment described herein.

FIG. 3 is a flowchart 40 for illustrating an interactive monitoring method by interactive monitoring system 12, according to an embodiment described herein.

At step 42, a generic event performed by said first user 16 may be detected by one or more of plurality of sensors 32 located in object 14. Object 14 may be located in proximity to first user 16 at location 26. Examples of object 14 may include a mechanical toy, a soft toy, an article constantly engaged with first user 16.

At step 44, a plurality of electronic units located on object 14 may be caused to be activated by microprocessor 34 based on said generic event performed by first user 16 detected by one or more of plurality of sensors 32. Plurality of electronic units may include first electronic unit, such as a camera 14E, second electronic unit which corresponds to a light display assembly 14A comprising a plurality of light units, third electronic unit which corresponds to one or more audio output devices, such as first set of speakers 14C, and fourth device which corresponds to one or more audio input devices, such as first microphone 14B.

At step 46, it may be checked whether battery level of remote display device 20 is sufficient. In an embodiment, when battery level of remote display device 20 is not sufficient, i.e. less than a threshold power level, low battery indicator beeper is activated, and control passes to step 58. In another embodiment, when battery level of remote display device 20 is sufficient, i.e. exceeds threshold power level, control passes to step 48. At step 58, battery of remote display device 20 may be charged to a level that exceeds threshold power level. Control passes to step 48.

At step 48, a FOV captured by first electronic unit of said activated plurality of electronic units may be communicated by object 14 to remote display device 20 over communication network 24B. FOV received from object 14 may be displayed at display screen of remote display device 20, such as a parent video monitor. In an embodiment, frame of remote display device 20 may resemble a design of a picture frame.

At step 50, a voice input generated by said first user 16 may be received by object 14 via one or more audio input devices, such as first microphone 14B. Voice input, for example, may be a query or merely a dialogue, such as "I am not feeling well," spoken by a young child, i.e. first user 16. At step 52, a response signal may be retrieved from memory unit 36 of object 14 based on received voice input. In an embodiment, microprocessor 34 may convert speech into text signal and may access memory unit 36 for retrieval of corresponding response dialogue, which is pre-stored in memory unit 36 while training interactive monitoring system 12. For example, microprocessor 34 may retrieve corresponding response dialogue "Don't worry kid! Mom is reaching in some time."

At step 54, response signal may be rendered by microprocessor 34 over an audio output device, such as first set of speakers 14C. At step 56, an alert notification may be generated by microprocessor 34 for remote display device 20 based on one or more critical events, for example first user 16 starts shouting or crying. At step 60, in response to alert notification, once second user 22 reaches within a pre-defined proximity, i.e. location 26, of first user 16, microprocessor 34 (FIG. 2) may be configured to deactivate plurality of electronic units for power saving.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An interactive monitoring system, comprising:
an object located in proximity to a first user, wherein said object includes a body portion, a head portion, and arm portions, a light display assembly mounted on said body portion, a first microphone located above said light display on said body portion, a first set of speakers mounted on a top end of said head portion, a first set of volume controls located on one of said arm portions, an image capturing device mounted on said head portion, wherein said object is a toy placed within a cradle holding said first user, wherein said object comprises a plurality of sensors configured to detect a generic event performed by said first user and cause a plurality of electronic units located on said object to activate based on said detected generic event performed by said first user; and
a remote display device having a display screen and a top portion, communicably coupled with said object over a communication network, wherein said top portion includes a power on/off switch, a second microphone, a second set of speakers, and a second set of volume controls, wherein said remote display device is configured to display a field-of-view (FOV) captured by a first electronic unit of said activated plurality of electronic units, wherein a second user associated with said remote display device communicates with said first user associated with said object, over said communication network.

2. The interactive monitoring system of claim 1, wherein said first electronic unit corresponds to said image capturing device or said first microphone, wherein plurality of sensors comprises at least motion activated camera sensor, voice sensor, and light sensor.

3. The interactive monitoring system of claim 1, wherein a second electronic unit of said activated plurality of electronic units corresponds to said light display assembly comprising a plurality of light units, wherein said plurality of light units are energized based on one of a plurality of pre-defined patterns.

4. The interactive monitoring system of claim 3, wherein a third electronic unit of said activated plurality of electronic units corresponds to one or more audio output devices, wherein said one or more audio output devices are configured to render one of a plurality of pre-defined music files, wherein a fourth device of said activated plurality of electronic units corresponds to one or more audio input devices, wherein said one or more audio input devices are configured to receive voice input provided by said first user.

5. The interactive monitoring system of claim 1, wherein said remote display device has a low battery indicator beeper which activates when battery level of said remote display device is less than a threshold power level.

6. The interactive monitoring system of claim 1, wherein said communication network is a long distance or short distance wireless network.

7. The interactive monitoring system of claim 1, wherein said first user is an infant, a toddler, a young child, or a user who needs continuous supervision, wherein said second user is a parent, a guardian, or a supervisor, wherein said object is a soft toy, or an article constantly engaged with said first user.

8. The interactive monitoring system of claim 1, wherein said object further comprises a microprocessor configured to receive a voice input generated by said first user, retrieve a response signal from a memory unit based on said received voice input and render said response signal over an audio output device.

9. The interactive monitoring system of claim 8, wherein said microprocessor is further configured to generate an alert notification for said remote display device based on one or more critical events.

10. The interactive monitoring system of claim 9, wherein said microprocessor is further configured to deactivate said plurality of electronic units when said object and said remote display device are within a pre-defined proximity.

11. The interactive monitoring system of claim 1, further comprising a remote-control device configured to control said plurality of electronic units located on said object.

12. An interactive monitoring system for monitoring children, comprising:
a) an object including a body portion, a head portion, and arm portions, wherein said object is a soft toy, said object including a light display assembly located on said body portion of said object, said light display assembly including a plurality of light emitting diodes (LEDs) configured to light up in predefined patterns, wherein said object further includes a first microphone located on said body portion, said first microphone being located above said light display assembly, said object including a first set of speakers mounted on a top end of said head portion, said object further including a first set of volume controls located on one of said arm portions of said object, wherein said head portion further includes a camera mounted thereon;
b) a cradle having said object placed therein;
c) a remote display device having a display screen and a top portion, wherein said top portion includes a power on/off switch, a second microphone, a second set of speakers and a second set of volume controls, wherein said remote display device is communicably coupled to said object over a long distance communication network;
d) a remote-control device communicably coupled with said object over a short distance communication network;
e) wherein said object further includes a transceiver configured to support a wireless communication to transmit or receive signals from said remote display device or said remote-control device;
f) wherein said object further includes sensors, said sensors including a motion sensor, a light sensor, and a camera sensor configured to detect a generic event performed by a user;
g) wherein said object further includes a microprocessor configured to activate a plurality of electronic units, wherein said microprocessor receives a voice input generated by said user through said first microphone, wherein microprocessor actuates said first set of speakers, wherein said microprocessor generates an alert notification received by said remote display device; and
h) wherein said object further includes a memory unit configured to temporarily store data, wherein said memory unit temporarily stores an energization pattern of said light display assembly, wherein said memory unit temporarily stores a plurality of pre-defined music files.

* * * * *